United States Patent
Cote et al.

(10) Patent No.: US 10,662,099 B2
(45) Date of Patent: May 26, 2020

(54) ASSEMBLY FOR SUPPORTING MIXED BIOFILM

(71) Applicant: GENERAL ELECTRIC COMPANY, Schenectady, NY (US)

(72) Inventors: Pierre Lucien Cote, Dundas (CA); Jeffrey Gerard Peeters, Oakville (CA)

(73) Assignee: BL Technologies, Inc., Minnetonka, MN (US)

( * ) Notice: Subject to any disclaimer, the term of this patent is extended or adjusted under 35 U.S.C. 154(b) by 0 days.

(21) Appl. No.: 15/550,255

(22) PCT Filed: Jun. 25, 2015

(86) PCT No.: PCT/US2015/037647
§ 371 (c)(1),
(2) Date: Aug. 10, 2017

(87) PCT Pub. No.: WO2016/209234
PCT Pub. Date: Dec. 29, 2016

(65) Prior Publication Data
US 2018/0044211 A1    Feb. 15, 2018

(51) Int. Cl.
*C02F 3/30* (2006.01)
*C02F 3/10* (2006.01)
(Continued)

(52) U.S. Cl.
CPC ............ *C02F 3/303* (2013.01); *B01D 63/023* (2013.01); *C02F 3/102* (2013.01); *C02F 3/1273* (2013.01);
(Continued)

(58) Field of Classification Search
CPC .......... C02F 3/303; C02F 3/208; C02F 3/302; C02F 3/102; C02F 3/1273;
(Continued)

(56) References Cited

U.S. PATENT DOCUMENTS 7,169,295 B2 †  1/2007  Husain et al.
7,300,571 B2   11/2007  Cote et al.
(Continued)

FOREIGN PATENT DOCUMENTS

WO    WO01/66474 A2    9/2001
WO    WO02/094421 A1   11/2002
(Continued)

OTHER PUBLICATIONS

"The membrane biofilm reactor (MBfR) for water and wastewater treatment: Principles, applications, and recent developments," Martin et al., Bioresource Technology, vol. 122, Oct. 2012, pp. 83-94.*

(Continued)

*Primary Examiner* — Fred Prince

(57) ABSTRACT

A bioreactor has a biofilm that receives a gas through a supporting membrane and another biofilm attached to an inert support. The first biofilm is aerated through the membrane and provides nitrification. The other biofilm has an anoxic or anaerobic zone and provides denitrification. A module useful in the bioreactor has cords potted in at least one potting head. Optionally, some or all of the cords have a gas transfer membrane. The module may provide inert supports, active gas transfer supports or a combination of both types of support. Multiple modules may be assembled together into a cassette, the cassette providing inert supports, active supports or a combination. The module or cassette may have an aerator for mixing or biofilm control.

14 Claims, 4 Drawing Sheets

(51) Int. Cl.
*C02F 3/20* (2006.01)
*B01D 63/02* (2006.01)
*C02F 3/12* (2006.01)
*C12M 1/04* (2006.01)
*C12M 1/12* (2006.01)

(52) U.S. Cl.
CPC .............. *C02F 3/208* (2013.01); *C02F 3/302* (2013.01); *C12M 23/24* (2013.01); *C12M 25/20* (2013.01); *B01D 2311/2665* (2013.01); *B01D 2313/23* (2013.01); *B01D 2313/26* (2013.01); *B01D 2315/06* (2013.01); *C02F 2203/006* (2013.01); *Y02W 10/15* (2015.05)

(58) Field of Classification Search
CPC ............ C02F 2203/006; B01D 63/023; B01D 2313/26; B01D 2313/23; B01D 2311/2665; B01D 2315/06; C12M 25/20; C12M 23/24; Y02W 10/15
USPC ............ 210/605, 620, 630, 150, 151, 221.1, 210/221.2, 615
See application file for complete search history.

(56) References Cited

U.S. PATENT DOCUMENTS

| | | | |
|---|---|---|---|
| 7,303,676 B2 | 12/2007 | Husain et al. | |
| 2002/0139747 A1* | 10/2002 | Gantzer | C02F 3/00 210/605 |
| 2003/0173706 A1 | 9/2003 | Rabie et al. | |
| 2005/0051481 A1* | 3/2005 | Husain | B01D 69/084 210/615 |
| 2005/0054087 A1* | 3/2005 | Cote | B01F 3/04269 435/299.1 |
| 2006/0037896 A1 | 2/2006 | Cote et al. | |
| 2006/0163157 A1* | 7/2006 | Cote | B01D 63/02 210/615 |
| 2007/0284294 A1* | 12/2007 | Jackson | C02F 3/10 210/150 |
| 2008/0314826 A1 | 12/2008 | Husain et al. | |
| 2012/0152832 A1* | 6/2012 | Johnson | C02F 3/02 210/615 |

FOREIGN PATENT DOCUMENTS

| | | | |
|---|---|---|---|
| WO | WO-2005/016498 A1 † | 2/2005 | |
| WO | WO 2008/130885 A2 * | 10/2008 | |
| WO | WO 2010/081228 A1 * | 7/2010 | |
| WO | WO 2014/130042 A1 * | 8/2014 | |
| WO | WO 2014/130043 A1 * | 8/2014 | |
| WO | WO2015/142586 A2 | 9/2015 | |

OTHER PUBLICATIONS

International Patent Application No. PCT/US2015/037647, International Search Report and Written Opinion dated Mar. 1, 2016.
Downing, L.S. and Nerenberg, R., "Performance and Microbial Ecology of the Hybrid Membrane Biofilm Process for Concurrent Nitrification and Denitrification of Wastewater", Water Science & Technology, 55(8-9): 355-362, 2007.
International Patent Application No. PCT/US2015/037647, International Preliminary Report on Patentability, dated Dec. 26, 2017.
Shanahan, J.W. and Semmens, M.J., "Multipopulation Model of Membrane-aerated Biofilm", Environmental Science & Technology, 38(11):3176-3183, 2004.
Syron, E. and Casey, E., "Membrane-Aerated Biofilms for High Rate Bio-treatment: Performance Appraisal, Engineering Principles, Scale-up, and Development Requirements", Environmental Science and Technology, 42(6): 1833-1844, 2008.
US Environmental Protection Agency, "Municipal Nutrient Removal Technologies Reference Document vol. 1—Technical Report", EPA 832-R-08-006, 2008.
Adams, N. et al. "A New Membrane-Aerated Biofilm Reactor (MABR) for Low Energy Treatment of Municipal Sewage", Singapore International Water Week, Singapore, Jun. 1-4, 2014.
Matsumoto, S. et al. "Modeling of Membrane-Aerated Biofilm: Effects of C/N Ratio, Biofilm Thickness and Surface Loading of Oxygen on Feasibility of Simultaneous Nitrifiation and Denitrification", Biochemical Engineering Journal, 37:98-107, 2007.
Baker, "Biofouting in membrane systems—A review," Jul. 30, 1998, Elsevier Science B.V., Desalination 118 (1998) 81-90.†
Downing, "Nitrogen Removal from Wastewater Using a Hybrid Membrane-Biofilm," Mar. 2010, Water Environment Research 82, 3, p. 195-201.†

\* cited by examiner
† cited by third party

ASSEMBLY FOR SUPPORTING MIXED BIOFILM

CROSS-REFERENCE TO RELATED APPLICATIONS

This application is a National Stage Entry of International Application No. PCT/US2015/037647, filed Jun. 25, 2015.

FIELD

This specification relates to wastewater treatment, to membrane biofilm reactors, and to supported biofilm devices and processes.

BACKGROUND

In a membrane biofilm reactor (MBfR), a membrane is used to both support a biofilm and to transport a gas to the biofilm. Membrane biofilm reactors were recently reviewed by Martin and Nerenberg in "The membrane biofilm reactor (MBfR) for water and wastewater treatment: Principles, applications, and recent developments" (Bioresour. Technol. 2012). Membrane-aerated biofilm reactors (MABR) are a subset of MBfRs in which an oxygen containing gas is used. MABRs were reviewed by Syron and Casey in "Membrane-Aerated Biofilms for High Rate Biotreatment: Performance Appraisal, Engineering Principles, Scale-up, and Development Requirements" (Environmental Science and Technology, 42(6): 1833-1844, 2008).

U.S. Pat. No. 7,169,295 describes a membrane supported biofilm reactor with modules having fine hollow fiber membranes. The membranes are made from dense wall polymethyl pentene (PMP) used in tows or formed into a fabric. The membranes are potted in a header of a module to enable oxygen containing gas to be supplied to the lumens of the hollow fibers. The reactor may be used to treat wastewater. Mechanical, chemical and biological methods are used to control the thickness of the biofilm. International Publication Number 2008/130885 describes a hybrid process with suspended biomass and a membrane supported biofilm.

SUMMARY OF THE INVENTION

This specification describes a bioreactor having two types of attached growth. One type of attached growth is a biofilm that receives a gas through a membrane. The other type of attached growth is a biofilm that is nourished only by way of one or more fluids that the biofilm is immersed in or passes through. A biofilm supporting media that supplies a gas through a membrane to the biofilm is referred to as an active support. A biofilm supporting media that does not supply a gas through a membrane to the biofilm is referred to as an inert support. The two types of support are combined in a reactor, optionally within a cassette of modules, or within a module. One or both types of support may be provided by a set of cords.

In a water treatment process described herein, a biofilm attached to a gas permeable membrane has an aerobic zone and is used primarily for nitrification. This biofilm receives oxygen through the membrane. Another biofilm attached to an inert support has an anoxic or anaerobic zone and is used primarily for denitrification and COD removal. The two types of biofilm can provide total nitrogen removal, for example using the nitrification-denitrification biological pathway or the nitritation-denitritation pathway.

The specification also describes a module having inert cords, or a mixture of active and inert supports such as cords, potted in at least one potting head. Cords are preferably independent of each other except in the potting head. A cord may be made up of one or more monofilament or multifilament yarns. Optionally, the module may have cords having one or more hollow fiber gas transfer membranes. A cord with a gas transfer membrane may be connected to a source of gas and provide an active support, or it may be used as an inert support without a source of gas. A cord without a gas transfer membrane may be used as an inert support. A module may have cords with or without gas transfers membranes or a combination of cords. A module having cords with gas transfer membranes may be configured such that some of these cords can receive a gas while others do not. In use, the module may support inert biofilms of the cords, or a mixture of inert and active biofilms.

A reactor has one or more modules with cords located in a tank adapted to hold water to be treated. Preferably, the reactor also has a gas delivery system connected to some, but not all, of the cords in the reactor. An alternative reactor has a gas delivery system connected to some or all of the cords in the reactor and the reactor also has inert supports, which may be provided in one or more of the modules or by another inert support system. A process for treating wastewater has steps of feeding water to the tank and supplying a gas to at least some of the cords in the reactor. In use, biofilms cover the cords.

DETAILED DESCRIPTION

Membrane supported biofilm modules can be made in various configurations. For example, flat sheet modules are described in WO 01/66474 A1. Modules using hollow fiber membranes in tows or woven into sheets are described in the Background section herein. A preferred module uses supports in the form of cords as described in WO 2014/130043. Modules using other configurations of biofilm supporting membranes, and modules of inert supports having these or other configurations, can be adapted to the devices and processes described herein.

Inert and active biofilm supports are combined in a single reactor. The reactor typically has a tank. The tank is adapted to receive wastewater to be treated, hold the wastewater while it is being treated, and discharge the wastewater. The reactor may be configured, for example, for batch, plug flow or continuously stirred reaction conditions, or a combination of conditions. While supports of different configurations may be mixed together, it is preferable to use supports having similar configurations for both the active and the inert supports. This provides similar packing density for the active and inert supports, and similar behavior in response to mixing and air scouring. The active and inert supports are preferably at least compatible, or can be made to be compatible. For example, the inert supports could be loose media such as sponges or plastic beads of the type used in moving bed bioreactors. However, since loose media might interfere with operation of a membrane supported biofilm, additional structures might be desirable, for example screens to separate the loose media from the membranes.

Figure 1:
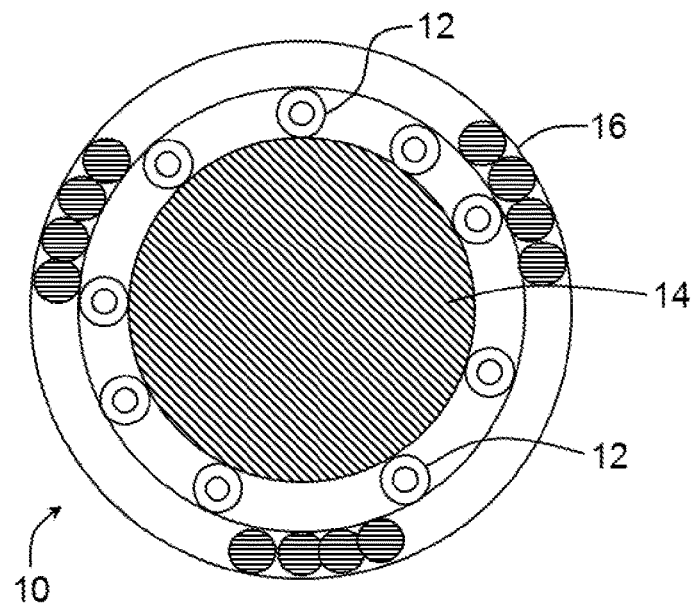
FIG. 1 is a schematic cross section of a cord.
Figure 2:
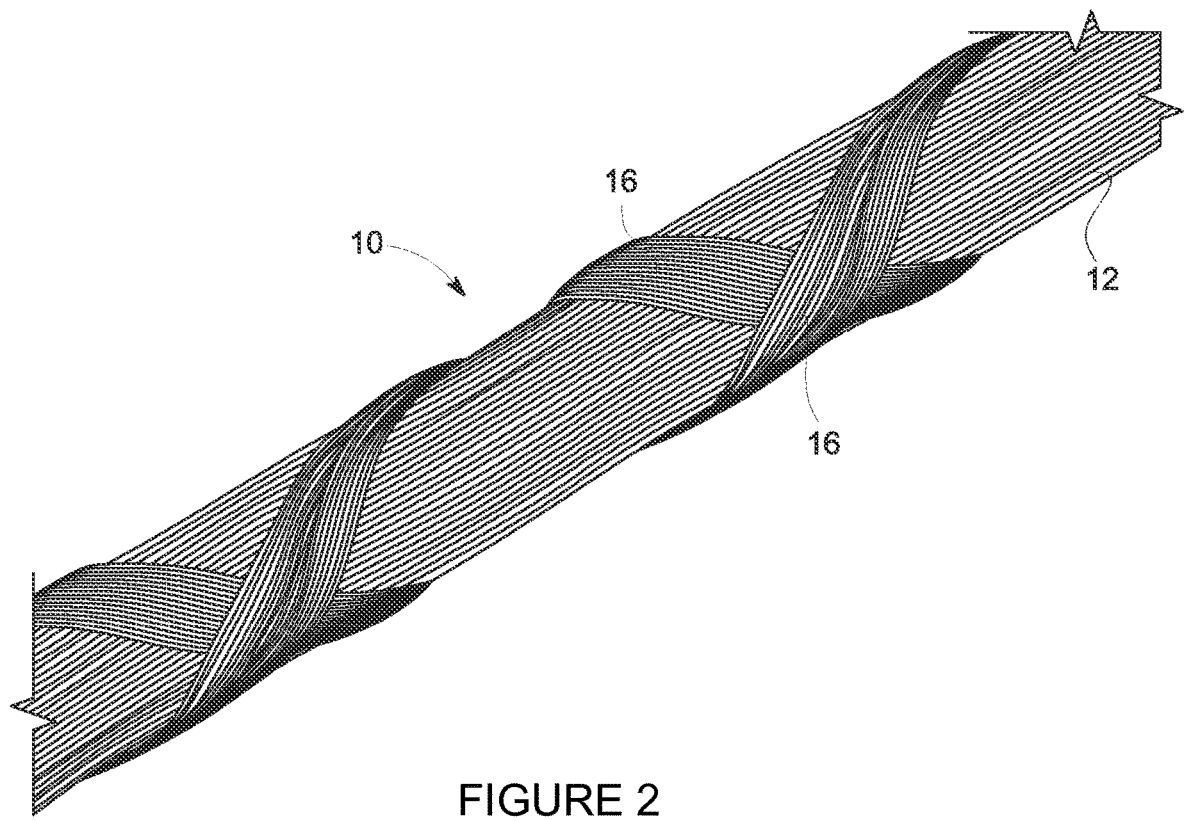
FIG. 2 is an isometric view of a cord.

In a preferred module, the active supports, and optionally the inert supports, are cords 10 as shown in FIGS. 1 and 2. A cord 10 contains gas-permeable hollow fibers 12. The hollow fibers 12 shown have a dense wall of oxygen-permeable polymer such a silicone or poly methyl pentene (PMP). PMP fibers may have an outside diameter less than 100 μm and a wall thickness of 15-20 μm. The hollow fibers 12 are distributed around the circumference of a core 14, which reinforces the cord 10 and supports the hollow fibers 12. The core 14 may be, for example, a yarn made of braided multi-filaments, non-braided multi-filament yarn, or a single monofilament yarn. Outer wrapping yarns 16 hold the hollow fibers 12 against the core 14 and may protect the hollow fibers 12 from abrasion. Alternatively, the hollow fibers 12 may be wrapped around the core 14 and the wrapping yarns 16 may be omitted. In the example of FIG. 2, the hollow fibers 12 completely surround the core 14. Alternatively, as in the example of FIG. 1, the hollow fibers 12 collectively cover only part of the circumference of the core 14.

The cord 10 is flexible so that it can sway in response to agitation provided for mixing and biofilm control. A bare cord 10 has a diameter of approximately 1-2 mm diameter. The diameter of the cord 10 increases by about 0.3 to 1.0 mm when the cord is covered with a biofilm. The biofilm fills in the gaps around the hollow fibers 12 and, to some extent, forms a film around the cord 10. The cord 10 does not have a flat and smooth surface but instead has an uneven surface, which provides a desirable environment for the biofilm to anchor to and helps prevent complete biofilm detachment during scouring events. Optionally, a cord may be made of another structure such as a single hollow monofilament, or a plurality of hollow monofilaments twisted, braided or otherwise formed into a yarn or thread. A single hollow monofilament, or other cords having hollow monofilaments of more than about 1 mm in diameter each, is optionally made of silicone (PDMS) in the case of an active support.

A cord with gas-permeable membranes may be an active support or an inert support depending on whether a gas is supplied to it or not. Alternatively, an inert support can be made by deleting the gas permeable hollow fibers, or by replacing them with essentially non-permeable hollow fibers or solid fibers. The replacement fibers are likely to be less expensive than gas permeable fibers, but using one type of cord may simplify manufacturing.

The relative surface area deployed for the active and inert supports can be determined based on relevant parameters such as influent characteristics, effluent concentration objectives, nitrification and denitrification rates, retention time, temperature, etc. For a specific case, the relative surface area can be estimated by modeling, for example using a wastewater treatment simulator such as GPS-X from Hydromantis Inc., or by conducting a pilot study. The relative surface areas of the active and inert supports may vary from 50:50 to 95:5.

A plurality of cords 10, for example 100 or more, may be made into a module generally in the manner of making an immersed hollow fiber membrane filtration module. At least one end of each of the cords 10 is potted in a block of a potting material such as thermoplastic or thermosetting resin. The solidified block of potting material may be called a potting head. A potting head may be sealed to a pan to form a header. The ends of the hollow fibers 12 of at least active cords 10 are made open to the inside of the header, for example by cutting them open after potting. The other ends of the cords 10 may be potted in another potting head, which might or might not be part of a header, with the ends of the gas transfer membranes 14 open or closed. Alternatively, the other ends of the cords 10 might be closed individually, or looped back and potted in the first potting head. A port in the header allows a gas to be optionally fed to the lumens of the hollow fibers 12. The gas may be fed to the hollow fibers 12 in a dead end manner or with exhaust through a second header. Alternatively, the port of a header may be closed to produce inert supports.

As one example, the cords 10 may be assembled into modules and cassettes according to the configuration of ZeeWeed 500™ immersed membrane filtration units, which are sold by GE Water & Process Technologies. Generally parallel rows of cords 10 are preferred, more preferably with the cords 10 generally evenly spaced in the rows and generally even spacing between the rows. To make the module, multiple rows of cords 10 are stacked on top of each other to form a bundle with adjacent rows spaced apart from each other, for example by a line of hot melt adhesive. The bundle is potted. After the potting material cures, the potting head is optionally cut to expose the open ends of the hollow fibers 12 and optionally sealed to a header pan. Several such modules may be attached to a common frame to form a cassette. Ports in the header pans, if any, are optionally manifolded together to receive gas from a shared inlet. Various useful techniques that may be used or adapted for making a module are described in U.S. Pat. Nos. 7,169,295, 7,300,571 and 7,303,676, US Publication 2003/01737006 A1 and International Publication Number WO 02/094421, all of which are incorporated by reference. Alternatively, other known techniques for making a hollow fiber membrane module may be adapted.

Figure 3:
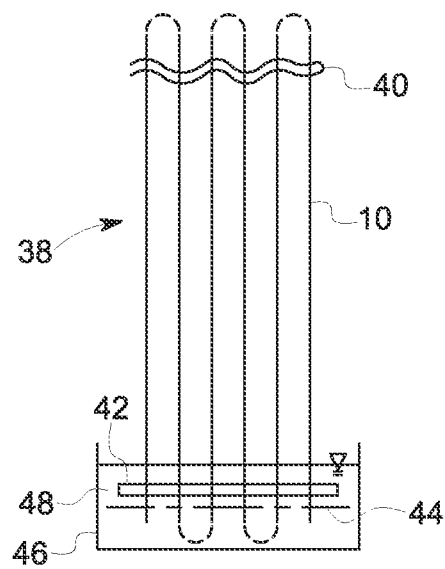
FIGS. 3 to 5 are schematic drawings of steps in a process for making a module comprising a plurality of cords.

Referring to FIG. 3, multiple cords 10, or an undulating cord 10 as shown, are laid out on a flat jig or drum to provide a row of generally parallel segments of cord 10 in a sheet 38. The segments of cord 10 may be kept evenly spaced from each other in the sheet 38, for example by a woven filament 40 or a strip of hot melt adhesive 42. Any open ends of the cords 10 may be sealed, for example by melting them with an iron or heated cutter along a sealing line 44. Multiple sheets 38 may be stacked on top of each other, preferably with the ends of adjacent sheets 38 separated from each other, for example by the hot melt adhesive 42 or by other spacers. The end of the set of sheets 38 is dipped in a potting mold 46 filled with a potting resin 48. The potting resin 48 may be, for example, polyurethane resin formulated flow around and seal to the cords 10. Active and inert cords 10 may be mixed together. For example, some sheets 38 may have active cords 10 while other sheets 38 have inert cords 10 made without hollow fiber membranes.

Figure 4:
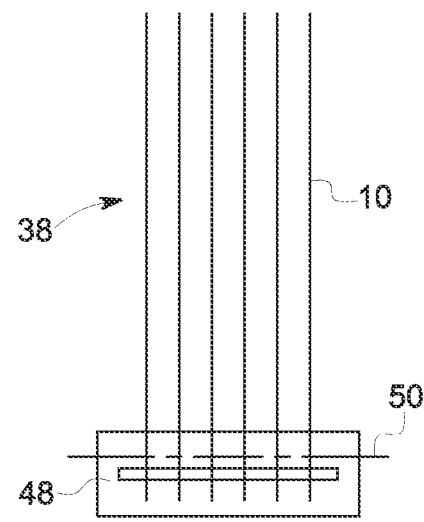

Referring to FIG. 4, the set of sheets 38 is removed from the potting mold 46 after the potting resin 48 is cured. To optionally expose open ends of the hollow fibers 12, the potting resin 48 is cut through along cutting line 50. The other end of the set of sheets 38 may be potted in the same manner. Optionally, both of the blocks of potting resin 48 may be cut to expose open ends of the hollow fibers 12.

Figure 5:
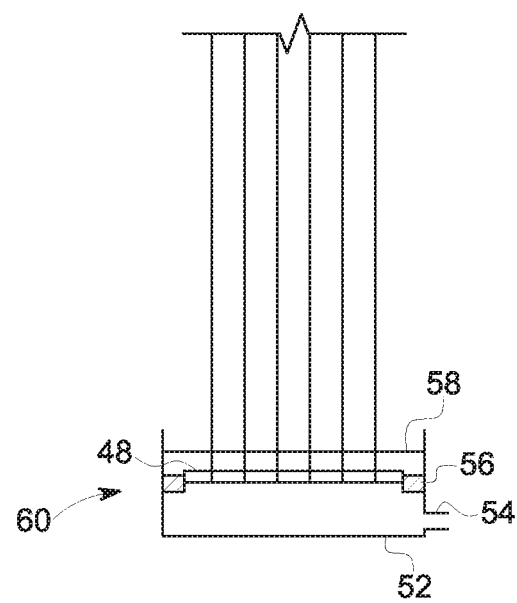

Referring to FIG. 5, a header 60 is formed by sealing the block of potting resin 48 to a header pan 52. The header pan 52 may be made, for example, of molded plastic. The header pan 52 has an outlet 54. The block of potting resin 48 may be held in the header pan 52 by an adhesive or a gasket 56 between the perimeter of the potting resin 48 and the header pan 52. Optionally, a second potting material 58 may be pored over the potting resin 48. The second potting material 58 may further seal the cords 10 or the potting resin 48 to the header pan 52, or may cushion the cords 10 where they exit from the header 60. A similar header 60 may be made at the other end of the set of sheets 38.

Figure 6:
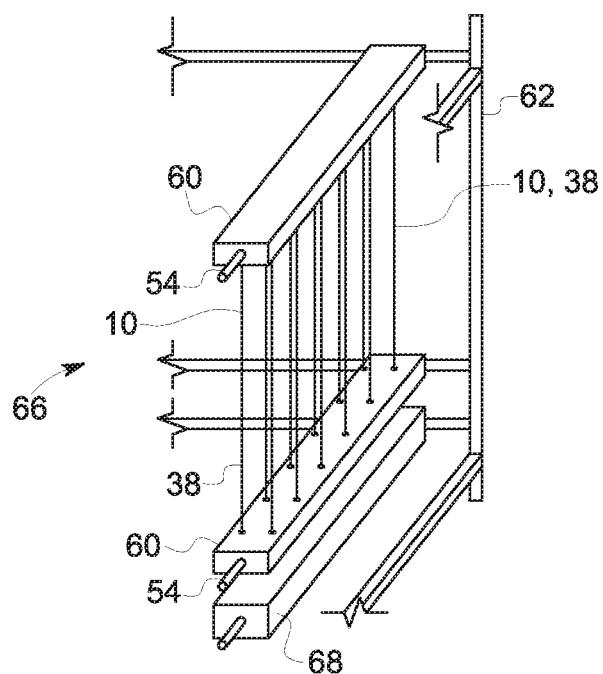
FIG. 6 is a schematic drawing of a module comprising a plurality of cords.

Referring to FIG. 6, a module 66 has two headers 60 with cords 10 extending between them. The headers 60 are preferably vertically aligned and held apart by a frame 62. The length of the cords 10 between opposing faces of the headers 60 may be slightly greater than the distance between the opposed faces of the headers 60. In this case, the cords 10 have some slack and can sway. The cords 10 are preferably not connected to each other between the headers 60. Although one cord 10 may contact another as it sways, the movement of a cord 10 is otherwise independent of other cords 10. Multiple modules 60 may be held in a common frame 62 to form a cassette. The frame 62 may also hold an aerator 68 near the bottom of a module 66. A module 66 with inert supports may be made in the same way and simply not provided with gas. Alternatively, a module 66 of inert supports may be made by potting cords 10 in a potting resin 48, but not opening the hollow fibers 12, if any. Optionally, the potting resin 48 may be attached to a header pan 52 such that the inert module 66 is interchangeable in the frame 62 with an active module 66, or a module with mixed active and inert cords 10. In various alternatives, a module 66 may have all inert cords 10, all active cords 10, or a mixture of active and inert cords 10. Inert cords 10 can be provided, for example, by cords 10 without hollow fibers 12, by cords 10 with hollow fibers 12 whose ends are closed, or by cords 10 with hollow fibers 12 that are not in communication with the header pan 52 that receives gas. In various alternatives, a cassette may have all modules 66 of active supports, all modules 66 of inactive supports, one or more modules 66 having a combination of active and inactive supports, or a mixture of modules 66 having active supports and modules 66 having inactive supports.

When used for wastewater treatment, the cords 10 are immersed in a bioreactor and a gas, typically air but possibly oxygen, hydrogen, methane or another gas, is fed through the lumens of any hollow fibers 12 used as active supports. A biofilm develops on the outside surface of the cords 10, and anchors itself by filling the gaps between filaments. The resulting membrane biofilm assembly has a generally circular cross section.

Modules 66 of the cords 10 may be deployed in a reactor by immersing them in an open tank. Gas sparging by way of bubbles produced below or near the bottom of the modules 66 can be provided at a low rate to renew the liquid around the cords 10. Gas sparging at a higher rate may be used to help control biofilm thickness either by the direct action of bubbles, by bubble wakes or bubble pressure effects on the biofilm, or by causing cords 10 mounted with slack to sway in the water to produce turbulence or contact between cords 10. Optionally, gas exhausted from the cords 10 may be recycled for use in gas sparging with or without being re-pressurized.

Figure 7:
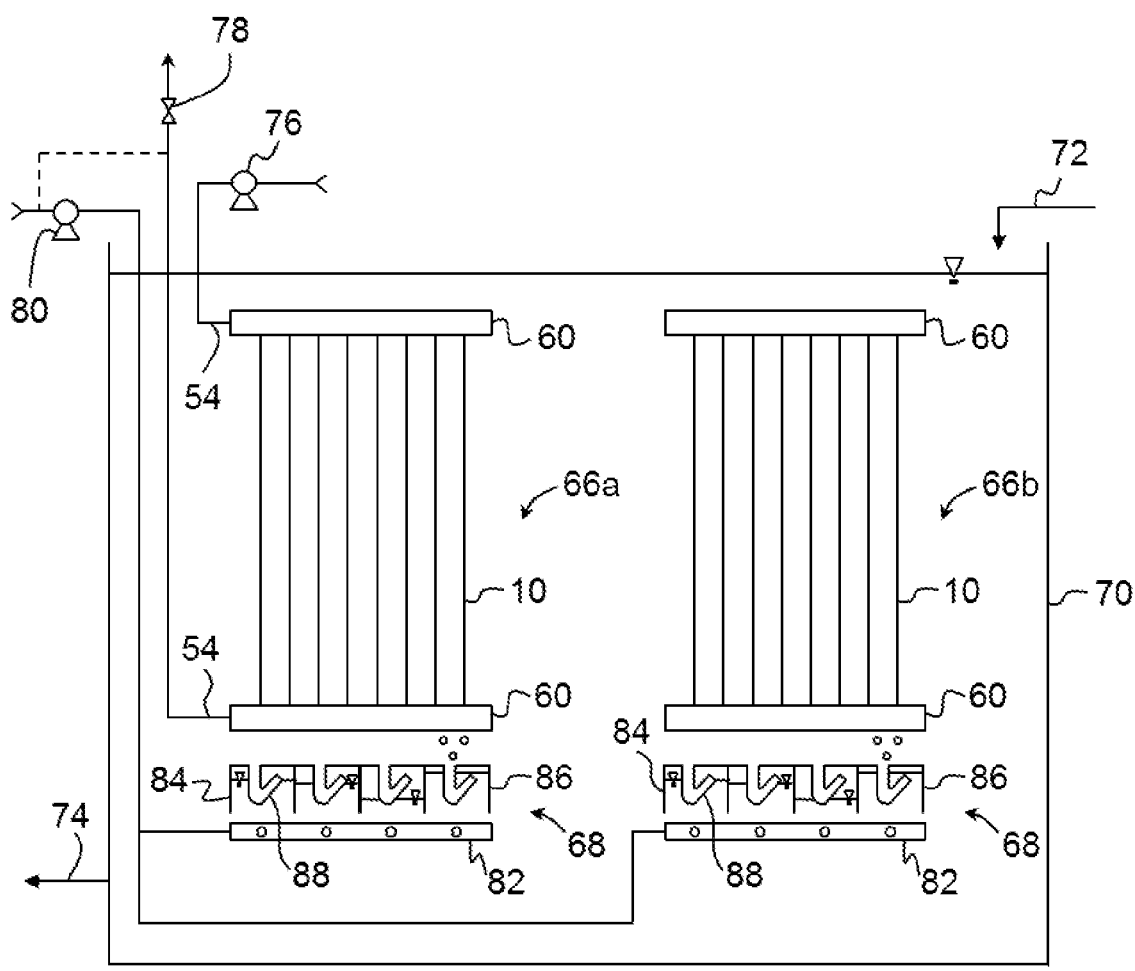
FIG. 7 is a schematic drawing of a reactor comprising the module of FIG. 6.

Referring to FIG. 7, two modules 66a and 66b are immersed in a tank 70. The modules 66a, 66b are made in the same way with cords 10 having hollow fibers 12. The tank 70 is filled with water to be treated from an inlet 72. Treated water is removed through an outlet 74. Optionally, water may recirculate from the outlet 74 to the inlet 72 to provide a flow of water through the module 66, mix the tank 70, or to maintain desired conditions in the tank 70. Air, or another gas, is blown into, or drawn out of, module 66a by a process gas blower 76. In the example shown, the gas is blown into a header 60, travels through the cords 10, and exhausted from the other header 60. A throttle valve 78 may be used to increase the gas pressure in the cords 10. A sparging gas blower 80 blows air or recycled exhaust gas from the modules 66a to the aerator 68 when required for mixing the tank 70 or controlling the thickness of the biofilm on the cords 10. Module 66a provides active supports. Module 66b is not connected to process gas blower 76 and provides inert supports. However, module 66b is connected to sparging gas blower 80.

Optionally, the aerator 68 may comprise a supply pipe 82 and a transducer 84. The transducer 84 collects gas ejected from the supply pipe in a pocket below a shell 86. The pocket of gas grows larger as gas is accumulated as shown in the first two compartments of the shell 86, counting from the left side of the shell 86. When the pocket of gas extends to the bottom of J shaped tube 88, as in the third compartment of the shell 86, the gas is released through the J shaped tube 88 as shown in the last compartment of the shell 86. In this way, large bursts of bubbles are released periodically without requiring a large volume of gas to be continuously pumped into the tank 70. Excessive scouring gas consumes energy and may disturb desirable anoxic or anaerobic conditions in the tank 70. Periodic large bursts of bubbles can be more effective for renewing the water around the cords 10 or removing biofilm from the cords 10 than the same amount of gas supplied as a continuous stream of bubbles.

Active and inert supports can be combined at the reactor level by combining inert and active cassettes in a reactor. Active and inert supports can alternatively by provided at the cassette level by combining inert and active modules in a cassette. Active and inert supports can alternatively be provided at the module level by combining inert and active cords in a module.

As the combination of supports occurs on a smaller scale, for example at or closer to the module level, the need for mixing to transport reactants from one type of support to the other is decreased. The preferred approach is to combine supports at the module level by having active and inert cords in the same module. For example, sheets of active cords may be alternated with sheets of inert cords in the assembly of the bundles as described above. When combining on the reactor level, it is easier to combine different types of supports. For example, a cassette of modules 66 with active cords as described above could be combined with inert supports typically used in IFAS reactors such as Cleartec™ sold by Jager of Bioweb™ sold by Entex Technologies.

Wastewater treatment benefits from the use of different types of microorganisms. Of particular importance is the synergistic work done under fully aerobic and anoxic conditions by autotrophic and heterotrophic bacteria. One application is nitrification by autotrophic bacteria under aerobic conditions complemented by denitrification by heterotrophic bacteria under anoxic conditions. Another application is the hydrolysis of complex organic molecules under anoxic/anaerobic conditions complemented by oxidation to $CO_2$ and $H_2O$ by heterotrophic bacteria under aerobic conditions.

A mix of active and inert biofilm supports allows these reactions (or others) to occur using fixed film supports located in the same tank. This can provide one or more of the benefits of fixed films processes relative to suspended growth processes such as, i) biomass retention generally unaffected by the operation of a clarifier or the occurrence of shock loading events, ii) reactors that can be run at lower mass loading rates with reduced excess biomass production, iii) sludge retention time independent of hydraulic retention time. Furthermore, pumping and mixing may be reduced relative to a suspended biomass reactor.

By providing separate aerobic and anoxic biofilms, the function of biofilm control (for example by air scouring) can be used to maintain a thin biofilm. This is in contrast to the use of a single biofilm to provide nitrification deep in the biofilm (e.g., close to the membrane surface) and denitrification in an outer anoxic layer. A single biofilm must be thick (i.e. >500 micron) to provide both nitrification and denitrification. The single biofilm approach is therefore faced with the difficulty of controlling the biofilm thickness to have the proper amounts of aerobic and anoxic biomass. A thick biofilm also creates a diffusion barrier for oxygen, nitrogen compounds or COD, which slows down the process. A thin biofilm helps provide relatively high aeration fluxes and reaction rates.

The active support provides a biofilm that is at least partially aerobic, and may be fully aerobic. However, the active supports do not transfer a significant amount of oxygen to the bulk liquid in the reactor. The bulk liquid in the reactor is under anoxic conditions. The biofilm on the inert support is at least partially anoxic. In a preferred reactor the active supports and the inert supports are similar in nature, deployed in similar (or identical) modules or cassettes and use the same or similar mixing and scouring equipment. This provides a compact and simple reactor that is capable of carrying out multi-step biochemical reactions such as nitrification-denitrification without having to recycle the wastewater between tanks or settle a suspended biomass.

International Publication Number WO 2014/130043 A1, Membrane Assembly for Supporting a Biofilm by General Electric Company, published on Aug. 28, 2014, is incorporated by reference. International Publication Number WO 2014/130042 A1, Wastewater Treatment with Membrane Aerated Biofilm and Anaerobic Digester by General Electric Company, published on Aug. 28, 2014, is incorporated by reference. International (WIPO) Application Number US2015/019943, Wastewater Treatment with Primary Treatment and MBR or MABR-IFAS Reactor, Filed on Mar. 11, 2015 by General Electric Company, is incorporated by reference.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art.

We claim:

1. A module comprising,
   at least one potting head; and,
   (i) one or more inert cords separately potted in the at least one potting head, wherein the one or more inert cords comprise a core and one or more fibers covering at least a portion of the core; or
   (ii) a combination of one or more inert biofilm supports and one or more active biofilm supports, separately potted in the at least one potting head, wherein the biofilm supports comprise a core and one or more fibers covering at least a portion of the core.

2. The module of claim 1 comprising a combination of one or more inert cords and one or more active cords potted in the at least one potting head.

3. The module of claim 1 comprising an aerator.

4. A cassette comprising,
   a frame;
   a first module comprising inert biofilm supports, the first module connected to the frame; and,
   a second module comprising gas transfer membrane biofilm supports, the second module connected to the frame wherein the inert biofilm supports are separated from the gas transfer membrane biofilm supports, and wherein the biofilm supports comprise a core and one or more fibers covering at least a portion of the core.

5. The cassette of claim 4 wherein the inert biofilm supports comprise cords.

6. The cassette of claim 4 wherein the first module and the second module each comprise inert biofilm supports and gas transfer membrane biofilm supports or the first module comprises only inert biofilm supports and the second module comprises only gas transfer membrane biofilm supports.

7. The cassette of claim 4 wherein the first module and the second module each comprises a header or potting head of similar size and shape.

8. The cassette of claim 4 wherein the first module is interchangeable in the frame with the second module.

9. A reactor comprising,
   a) a tank;
   b) an active biofilm support media in the tank; and,
   c) an inert biofilm support media in the tank
   wherein the active biofilm support media supports a different biofilm than the inert biofilm support media, and
   wherein the active support media comprises hollow fiber gas permeable membranes.

10. The reactor of claim 9 wherein the inert biofilm support media is a fixed media.

11. The reactor of claim 9 wherein the inert biofilm support media comprises a plurality of cords.

12. A process for treating wastewater comprising steps of,
    contacting the wastewater with aerobic biofilms; and
    contacting the wastewater with anoxic or anaerobic biofilms,
    wherein the aerobic biofilms and the anoxic or anaerobic biofilms are located in a common tank but separate and attached to different supports, wherein the supports for the aerobic biofilms comprise gas permeable membranes having inside surfaces and outside surfaces; and,
    providing oxygen to the inside surfaces of the gas permeable membranes such that the oxygen travels to the aerobic biofilms through the gas permeable membranes, wherein the aerobic biofilms are attached to the outside surfaces of the gas permeable membranes.

13. The process of claim 12 comprising steps of maintaining the aerobic biofilms and the anoxic or anaerobic biofilms at a thickness of less than 0.5 mm.

14. The process of claim 12 wherein the anoxic or anaerobic biofilms are dispersed among the aerobic biofilms.

* * * * *